US00PP31801P2

(12) United States Plant Patent
Stemkens

(10) Patent No.: US PP31,801 P2
(45) Date of Patent: May 26, 2020

(54) ***ERYSIMUM* PLANT NAMED 'ERFZ0005'**

(50) Latin Name: *Erysimum linifolium*
Varietal Denomination: ERFZ0005

(71) Applicant: SYNGENTA CROP PROTECTION AG, Basel (CH)

(72) Inventor: Henricus Godefridus Wilhelmus Stemkens, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/501,773

(22) Filed: Jun. 5, 2019

(51) Int. Cl.
*A01H 5/02* (2018.01)
*A01H 6/20* (2018.01)

(52) U.S. Cl.
USPC ..... Plt./263.1

(58) Field of Classification Search
USPC ..... Plt./263.1
CPC ..... A01H 5/02; A01H 6/20
See application file for complete search history.

*Primary Examiner* — Annette H Para
(74) *Attorney, Agent, or Firm* — Dale Skalla

(57) ABSTRACT

A new *Erysimum* plant named 'ERFZ0005' particularly distinguished by the orange lilac flower color, grey green foliage color, rounded and semi-erect plant habit with good branching, and is very early to flower.

1 Drawing Sheet

Latin name of the genus and species of the plant claimed: *Erysimum linifolium.*

Varietal denomination: 'ERFZ0005'.

BACKGROUND OF THE NEW PLANT

The present invention comprises a new *Erysimum*, botanically known as *Erysimum linifolium*, and hereinafter referred to by the variety name 'ERFZ0005'.

'ERFZ0005' is a product of a planned breeding program. The new cultivar 'ERFZ0005' has an orange lilac flower color, grey green foliage color, rounded and semi-erect plant habit with good branching, and is very early to flower.

'ERFZ0005' originates from a hybridization made in a greenhouse in April 2014 in Enkhuizen, The Netherlands. The female parent was a proprietary plant identified as 'P1630-56', unpatented, with mauve flower color, fewer branches, and overall smaller size than that of 'ERFZ0005'.

The male parent of 'ERFZ0005' is an unknown plant from the whole population of *Erysimum*. The resultant seed was sown in September 2014 in a greenhouse in Enkhuizen, The Netherlands.

'ERFZ0005' was selected as one flowering plant within the progeny of the stated cross in March 2015 in Enkhuizen, The Netherlands. It is a sister plant of the same cross as 'ERFZ0004'.

The first act of asexual reproduction of 'ERFZ0005' was accomplished when vegetative cuttings were propagated from the initial selection in May 2015 in a controlled environment in Enkhuizen, The Netherlands.

BRIEF SUMMARY OF INVENTION

Horticultural examination of plants grown from cuttings of the plant initiated in May 2015 in Enkhuizen, The Netherlands, and continuing thereafter, has demonstrated that the combination of characteristics as herein disclosed for 'ERFZ0005' are firmly fixed and are retained through successive generations of asexual reproduction.

'ERFZ0005' has not been observed under all possible environmental conditions. The phenotype may vary significantly with variations in environment such as temperature, light intensity, and day length.

A Plant Breeder's Right for this cultivar has not yet been applied for. 'ERFZ0005' has not been made publicly available prior to the effective filing date of this application, notwithstanding any disclosure that may have been made less than one year prior to the effective filing date of this application by the inventor or another who obtained 'ERFZ0005' directly from the inventor.

The following traits have been repeatedly observed and are determined to be basic characteristics of the new variety. The combination of these characteristics distinguishes this *Erysimum* as a new and distinct variety

BRIEF DESCRIPTION OF THE PHOTOGRAPHS

Figure 1:
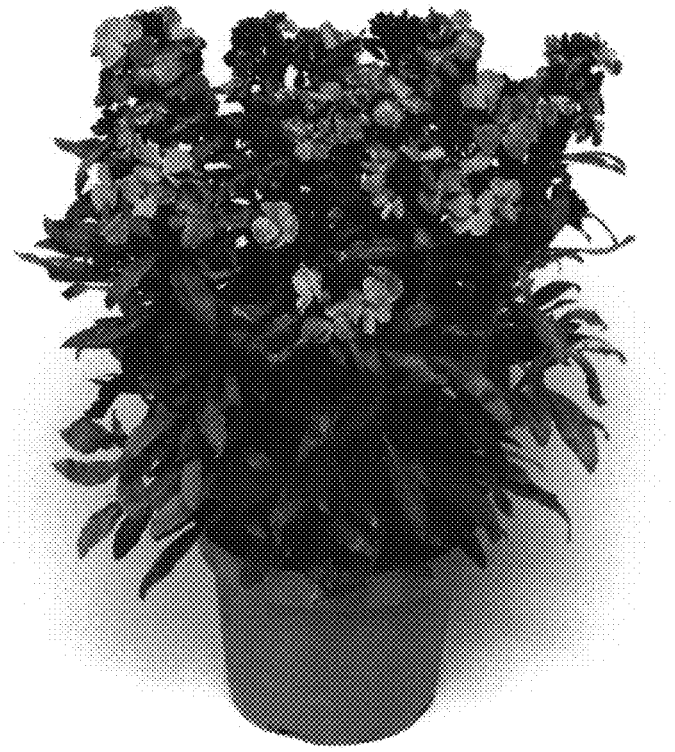
Figure 2:
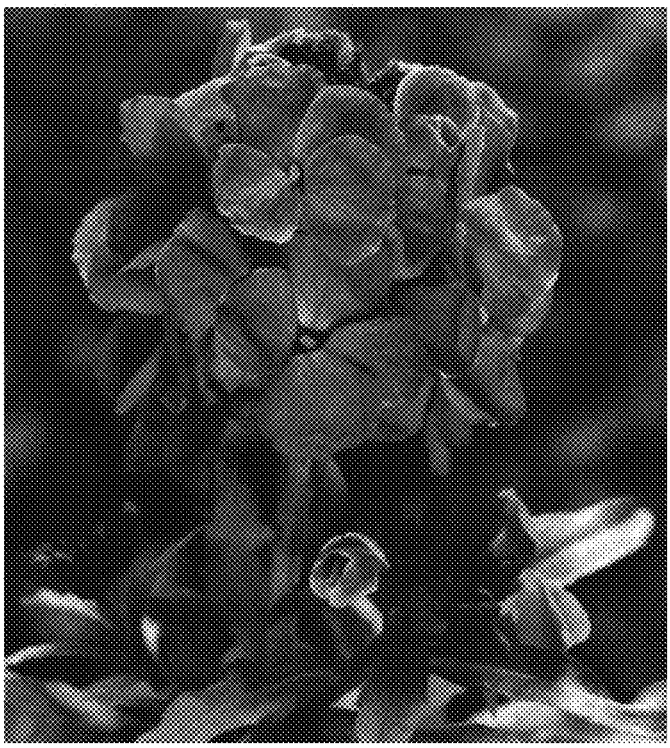

The accompanying photographic drawings show typical flower and foliage characteristics of 'ERFZ0005' with colors being as true as possible with an illustration of this type. The photographic drawings show in FIG. 1 a flowering plant of the new variety and in FIG. 2 a close-up of a flower and buds.

DETAILED BOTANICAL DESCRIPTION

The plant descriptions, measurements and aforementioned photographs were taken in Andijk, The Netherlands in March 2018 under natural light. These plants were growing in an indoor trial under natural light in Andijk, The Netherlands. The plants were about 18 weeks of age.

Color chart used: Royal Horticultural Society Colour Chart (R.H.S.) 2001

TABLE 1

DIFFERENCES BETWEEN THE NEW VARIETY 'ERFZ0005' AND A SIMILAR VARIETY

| | 'ERFZ0005' | 'ERFZ0003' (U.S. Plant Pat. No. 29,331) |
|---|---|---|
| Natural flowering response: | Earlier | Later |
| Plant habit: | Shorter when plants start to flower | Taller when plants start to flower |
| Foliage color: | Lighter grey green | Deeper grey green |
| Flower spike: | Very short | Becomes longer on mature plants |
| Flower color: | Orange lilac | Mauve |

Plant:

*Form, growth and habit*.—Compact and tightly mounded, good flowering on short peduncles at more mature stage.

*Plant height*.—22-28.0 cm.

*Plant height (inflorescence included)*.—39-44.0 cm.

*Plant width*.—About 19.0 cm.

Roots:

*Number of days to initiate roots*.—About 7 days at about 18 degrees C.

*Number of days to produce a rooted cutting*.—About 4 weeks at 18 degrees C.

*Type*.—Fine, fibrous, free branching.

*Color*.—RHS N155B.

Foliage:

*Arrangement*.—Alternate.

*Immature, leaf color, upper surface*.—RHS 147B.

*Immature, leaf color, lower surface*.—RHS 137C.

*Mature, leaf color, upper surface*.—RHS 147B.

*Mature, leaf color, lower surface*.—RHS 137C.

*Length*.—5.4-6.0 cm.

*Width*.—0.7-0.9 cm.

*Shape*.—Narrowly oblanceolate to ensiform.

*Base shape*.—Cuneate.

*Apex shape*.—Acute to abruptly acute.

*Margin*.—Entire.

*Texture, upper surface*.—Bifid T-shaped hairs.

*Texture, lower surface*.—Bifid T-shaped hairs.

*Color of veins, upper surface*.—RHS 143A.

*Color of veins, lower surface*.—RHS 143B.

*Veination pattern*.—Pinnate.

*Petiole colour*.—RHS 144B.

*Length*.—0.5-0.7 cm.

*Diameter*.—0.2 cm.

*Texture*.—Smooth.

Stem:

*Color of stem*.—RHS 144A.

*Length of stem*.—16-18.0 cm.

*Diameter*.—0.4 cm.

*Length of internodes*.—1.4 cm.

*Texture*.—Smooth.

*Colour of peduncle*.—RHS 144A.

*Length of peduncle*.—9.0-19.0 cm.

*Diameter of peduncle*.—0.3-0.4 cm.

*Texture*.—Smooth.

*Color of pedicel*.—RHS 144B.

*Length of pedicel*.—0.3 cm.

*Diameter of pedicel*.—0.05 cm.

*Texture*.—Smooth.

Inflorescence:

*Type*.—Single, cruciform, composed of 4 petals; flowers held above the plant, relatively long peduncles on more mature plants.

*Natural flowering season*.—March to October in The Netherlands.

*Quantity of inflorescences per plant*.—14-25 with open flowers and 12-18 immature ones.

*Lastingness of individual blooms on the plant*.—About 4 days.

*Fragrance*.—None.

Bud (just before opening/showing color):

*Color*.—Some RHS 155C and some closer to RHS 84C.

*Length*.—0.9 cm.

*Width*.—0.4-0.5 cm.

*Shape*.—Oblong.

Corolla:

Immature inflorescence:

*Diameter*.—1.4-1.6 cm.

*Color of petals, upper surface*.—RHS 168C.

*Color of petals, lower surface*.—RHS 168B.

Mature inflorescence:

*Flower diameter*.—1.5-1.6 cm.

*Depth*.—1.2-1.4 cm.

*Petal color, upper surface*.—RHS 184D.

*Petal color, lower surface*.—RHS 184C.

*Length of petal*.—0.7-0.8 cm.

*Width of petal*.—0.5-0.6 cm.

*Shape*.—Spathulate.

*Apex shape*.—Slightly retuse.

*Petal base*.—Acuminate.

*Margin*.—Entire.

*Petal texture, upper surface*.—Smooth.

*Petal texture, lower surface*.—Smooth.

Calyx:

*Quantity*.—4 sepals.

*Color, upper surface*.—RHS 137B.

*Color, lower surface*.—RHS 137B.

*Sepals*.—

*Length*.—0.5 cm.

*Width*.—0.3 cm.

*Shape*.—Broadly oblong.

*Apex shape*.—Obtuse.

*Base*.—Cuneate.

*Margins*.—Entire.

*Texture, upper/inner surface*.—Glabrous.

*Texture, lower/outer surface*.—Smooth.

Reproductive organs:

Gynoecium:

*Pistil quantity*.—1.

*Length*.—0.7 cm.

*Style color*.—RHS 145C.

*Style length*.—0.45-0.5 cm.

*Style texture*.—Heavily covered with bifid hairs as to appear much lighter in color.

*Stigma color*.—RHS 145C.

*Stigma shape*.—Oval to disc-shaped and a cleft down the center.

*Stigma texture*.—Grainy looking.

*Ovary color*.—Not developed enough to observe.

Androecium:

*Stamens, quantity*.—6.

*Color of filaments*.—RHS 160C and somewhat translucent.

*Length filaments*.—0.6 cm.
*Anther color*.—RHS 18A.
*Anther length*.—0.3 cm.
*Anther shape*.—Oblong.
*Color of pollen*.—RHS 18B.
*Pollen amount*.—Normal.
*Fertility/seed set*.—Has not been determined to date.
*Disease/pest resistance*.—Has not been determined to date.

What is claimed is:

1. A new and distinct variety of *Erysimum* plant named 'ERFZ0005' substantially as illustrated and described herein.

* * * * *